US009345391B2

(12) United States Patent
Kuriyama

(10) Patent No.: US 9,345,391 B2

(45) Date of Patent: May 24, 2016

(54) CONTROL DEVICE, ENDOSCOPE APPARATUS, APERTURE CONTROL METHOD, AND INFORMATION STORAGE MEDIUM

(75) Inventor: Naoya Kuriyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 817 days.

(21) Appl. No.: 13/360,996

(22) Filed: Jan. 30, 2012

(65) Prior Publication Data

US 2012/0197079 A1 Aug. 2, 2012

(30) Foreign Application Priority Data

Jan. 31, 2011 (JP) ................................ 2011-017481

(51) Int. Cl.

*A61B 1/045* (2006.01)
*A61B 1/00* (2006.01)
*G02B 23/24* (2006.01)

(52) U.S. Cl.

CPC ............. *A61B 1/045* (2013.01); *A61B 1/00096* (2013.01); *G02B 23/2476* (2013.01)

(58) Field of Classification Search

CPC ...................................................... A61B 1/045
USPC ......................................... 348/346, 347, 354
See application file for complete search history.

(56) References Cited

U.S. PATENT DOCUMENTS

| | | | | |
|---|---|---|---|---|
| 5,623,706 | A * | 4/1997 | Kosako | 396/67 |
| 8,355,047 | B2 * | 1/2013 | Takeuchi | 348/169 |
| 2004/0151486 | A1 * | 8/2004 | Goris et al. | 396/147 |
| 2006/0216013 | A1 * | 9/2006 | Kueblbeck et al. | 396/121 |
| 2008/0252773 | A1 | 10/2008 | Oishi | |
| 2009/0310229 | A1 * | 12/2009 | Yang et al. | 359/694 |
| 2010/0045849 | A1 * | 2/2010 | Yamasaki | 348/349 |
| 2010/0141752 | A1 * | 6/2010 | Yamada et al. | 348/79 |
| 2010/0208126 | A1 * | 8/2010 | Uenishi | 348/345 |

FOREIGN PATENT DOCUMENTS

| | | |
|---|---|---|
| JP | H07-143291 A | 6/1995 |
| JP | 2004-258360 | 9/2004 |
| JP | 2008-165044 A | 7/2008 |
| JP | 2008-262001 | 10/2008 |
| JP | 2009-240531 | 10/2009 |
| JP | 2010-127995 | 6/2010 |

OTHER PUBLICATIONS

Japanese Office Action dated Sep. 2, 2014 from related Japanese Patent Application No. 2011-017481, together with an English language translation.

* cited by examiner

*Primary Examiner* — Christopher S Kelley
*Assistant Examiner* — Jonathan Messmore
(74) *Attorney, Agent, or Firm* — Scully, Scott, Murphy & Presser, P.C.

(57) ABSTRACT

A control device includes an image acquisition section that acquires an image of an object captured by an imaging optical system of an endoscope apparatus, a determination section that determines whether or not an observation area is in focus based on a pixel value of each pixel within the image of the object, the observation area being an observation target area within the image of the object, and an aperture control section that controls an aperture of the imaging optical system based on a result of the determination.

18 Claims, 12 Drawing Sheets

CONTROL DEVICE, ENDOSCOPE APPARATUS, APERTURE CONTROL METHOD, AND INFORMATION STORAGE MEDIUM

Japanese Patent Application No. 2011-017481 filed on Jan. 31, 2011, is hereby incorporated by reference in its entirety.

BACKGROUND

The present invention relates to a control device, an endoscope apparatus, an aperture control method, an information storage medium, and the like.

An endoscope has been widely used in the field of medical treatment. The endoscope is configured so that an elongated scope that is provided with a CCD or the like at its end is inserted into the body cavity of a subject, and an image of the inside of the body cavity is captured to observe a tumor or the like. The endoscope captures an image while illuminating an object inside the body cavity of the subject. It is desired to provide an image that is in focus over a range in which illumination light is applied at an intensity sufficient for observation. Specifically, it is desired to provide a deep-focus image in which a near object and a distant object are included within the depth of field of the imaging optical system.

SUMMARY

According to one aspect of the invention, there is provided a control device comprising:

an image acquisition section that acquires an image of an object captured by an imaging optical system of an endoscope apparatus;

a determination section that determines whether or not an observation area is in focus based on a pixel value of each pixel within the image of the object, the observation area being an observation target area within the image of the object; and an aperture control section that controls an aperture of the imaging optical system based on a result of the determination.

According to another aspect of the invention, there is provided an endoscope apparatus comprising the above control device.

According to another aspect of the invention, there is provided an aperture control method comprising:

acquiring an image of an object captured by an imaging optical system;

determining whether or not an observation area is in focus based on a pixel value of each pixel within the image of the object, the observation area being an observation target area within the image of the object; and controlling an aperture of the imaging optical system based on a result of the determination.

According to another aspect of the invention, there is provided an information storage medium storing a program that causes a computer to function as:

an image acquisition section that acquires an image of an object captured by an imaging optical system of an endoscope apparatus;

a determination section that determines whether or not an observation area is in focus based on a pixel value of each pixel within the image of the object, the observation area being an observation target area within the image of the object; and an aperture control section that controls an aperture of the imaging optical system based on a result of the determination.

DESCRIPTION OF EXEMPLARY EMBODIMENTS

Figure 1:
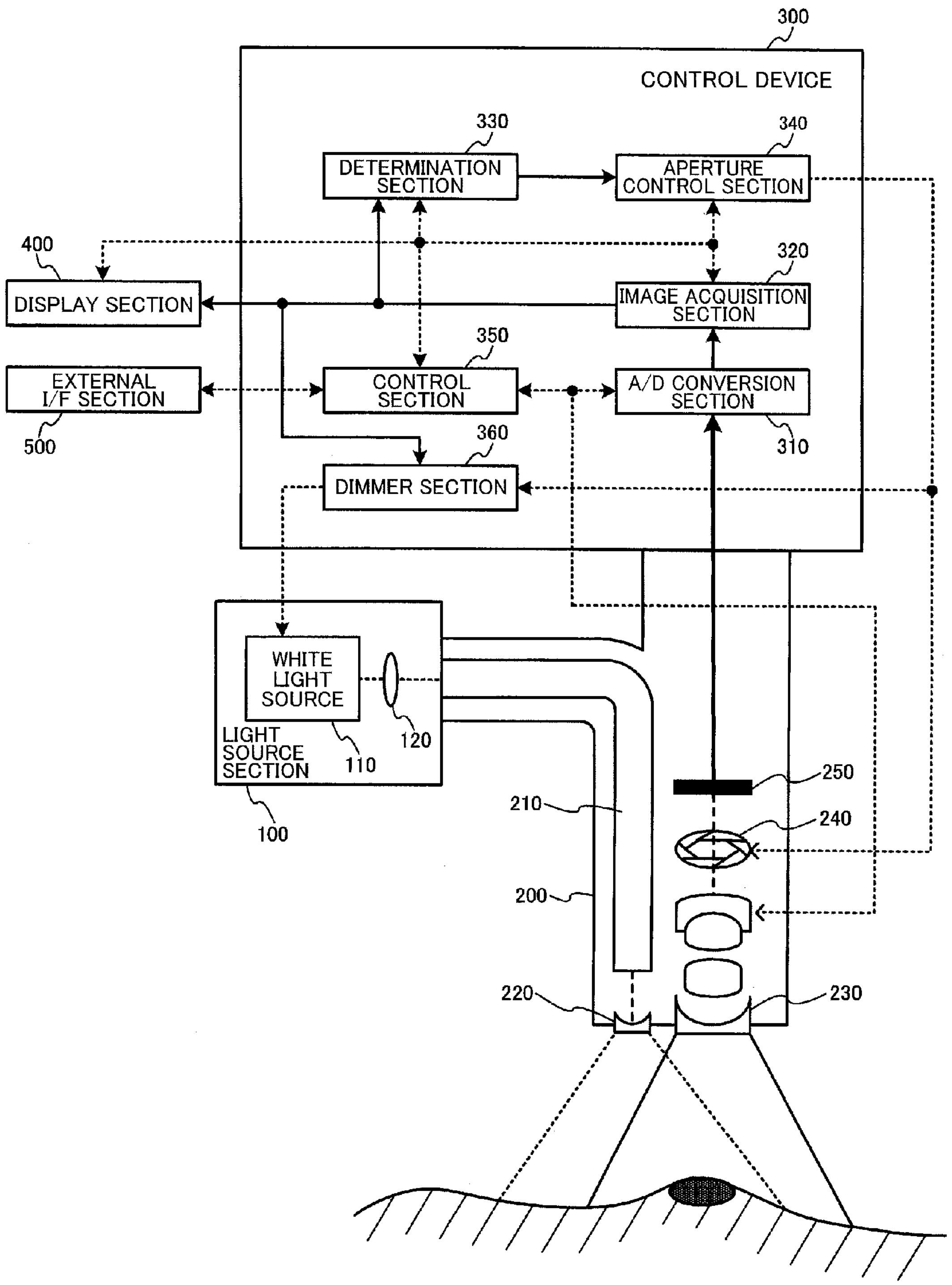
FIG. 1 shows a configuration example of an endoscope apparatus according to one embodiment of the invention.

In recent years, an increase in quality of an endoscope image has been desired to improve the diagnostic accuracy, and an imaging element having a larger number of pixels has been used. Since the size of the permissible circle of confusion of the imaging optical system decreases as the pixel pitch of the imaging element decreases due to an increase in the number of pixels, the depth of field of the imaging optical system decreases. This makes it difficult to acquire an image in which a near object and a distant object are in focus. The depth of field can be increased by closing the aperture. However, the resolution decreases due to a small aperture blur when closing the aperture.

For example, JP-A-2009-240531 discloses a method that acquires an image suitable for observation (i.e., an image that is in focus in its entirety). The method disclosed in JP-A-2009-240531 synthesizes an image that is in focus in its entirety from images captured at a plurality of in-focus object plane positions.

Several aspects of the invention may provide a control device, an endoscope apparatus, an aperture control method, a program, and the like that implement deep focus while suppressing a decrease in resolution.

According to one embodiment of the invention, there is provided a control device comprising:

an image acquisition section that acquires an image of an object captured by an imaging optical system of an endoscope apparatus;

a determination section that determines whether or not an observation area is in focus based on a pixel value of each pixel within the image of the object, the observation area being an observation target area within the image of the object; and an aperture control section that controls an aperture of the imaging optical system based on a result of the determination.

According to one aspect of the invention, whether or not the observation area is in focus is determined based on the pixel value of each pixel within the image of the object, and the aperture of the imaging optical system is controlled based on the result of the determination. This makes it possible to implement deep focus while suppressing a decrease in resolution.

Exemplary embodiments of the invention are described below. Note that the following exemplary embodiments do not in any way limit the scope of the invention laid out in the claims. Note also that all of the elements of the following exemplary embodiments should not necessarily be taken as essential elements of the invention.

1. Outline

An outline of several embodiments of the invention is described below. It has become difficult to implement deep focus while suppressing a decrease in resolution along with a decrease in pixel pitch.

A range in which a point light source forms an image in the image plane via an optical system is referred to as a circle of confusion. A range in which the circle of confusion is considered to be a point (i.e., a range in the image plane that is considered to be in focus) is referred to as a permissible circle of confusion. The size of the circle of confusion becomes a minimum when the point light source is positioned at the in-focus object plane position, and increases as the point light source moves away from the in-focus object plane position. The depth of field is the range of the point light source within which the circle of confusion is included in the permissible circle of confusion. Therefore, the depth of field decreases when the size of the permissible circle of confusion decreases due to a decrease in pixel pitch.

The depth of field can be increased by closing the aperture. However, a small aperture blur (diffraction limit) occurs when closing the aperture. Since the effects of a small aperture blur increase as the size of the permissible circle of confusion decreases, it becomes difficult to implement deep focus and high resolution at the same time as the pixel pitch decreases. For example, a current endoscope is designed to have an aperture value (e.g., aperture value is F-number) that minimizes a decrease in resolution due to a small aperture blur while implementing deep focus. However, a desired depth of field differs depending on the observation target (e.g., a hollow tubular observation target or flat observation target). Therefore, when the aperture value is fixed, a decrease in resolution due to a small aperture blur occurs even if the depth of field is narrow.

In recent years, an imaging optical system that implements magnifying observation has been increasingly desired in order to accurately diagnose a lesion. An imaging optical system of an endoscope that implements magnifying observation tends to have a reduced depth of field.

In order to deal with the above problems, several embodiments of the invention provide a desired depth of field while minimizing a decrease in resolution due to a small aperture blur by adaptively controlling the aperture corresponding to the observation area. Specifically, the observation area is divided into segmented observation areas A1 to A5 (see FIG. 3B), and whether or not the segmented observation areas A1 to A5 are in focus is determined. The aperture value of the imaging optical system is adjusted based on the in-focus determination results so that the segmented observation areas A1 to A5 are included within the depth of field. This makes it possible to provide an image in which the observation target object is in focus while minimizing a decrease in resolution. Moreover, since it is unnecessary to reduce the frame rate, a flicker or the like does not occur. Therefore, an increase in burden on the user does not occur.

2. First Embodiment

2.1. Endoscope Apparatus

FIG. 1 shows a configuration example of an endoscope apparatus according to a first embodiment of the invention. The endoscope apparatus includes a light source section 100, an imaging section 200 (insertion section), a control device 300 (signal processing section), a display section 400, and an external I/F section 500. Note that the configuration of the endoscope apparatus is not limited to the configuration shown in FIG. 1. Various modifications may be made, such as omitting some of the elements or adding other elements.

The light source section 100 includes a white light source 110 and a condenser lens 120. The white light source 110 emits white light. The condenser lens 120 focuses the white light emitted from the white light source 110 on a light guide fiber 210 (described below).

The imaging section 200 is formed to be elongated and flexible (i.e., can be curved) so that the imaging section 200 can be inserted into a body cavity or the like. The imaging section 200 includes the light guide fiber 210, an illumination lens 220, an objective lens 230, a variable aperture 240, and an imaging element 250. The light guide fiber 210 guides the light that has been focused by the light source section 100 to the end of the imaging section 200. The illumination lens 220 diffuses the light that has been guided to the end of the light guide fiber 210, and applies the diffused light to an observation target. The objective lens 230 focuses reflected light from the observation target on the imaging element 250. The variable aperture 240 is disposed in the optical path between the objective lens 230 and the imaging element 250. The variable aperture 240 controls the intensity of light focused on the imaging element 250 based on an aperture control signal output from an aperture control section 340 (described below). The imaging element 250 outputs an analog signal based on the detected reflected light to an A/D conversion section 310 (described below).

The objective lens 230 has a magnification function that changes the magnification of the optical system. The user can change the magnification of the optical system at an arbitrary timing by operating the external I/F section 500. More specifically, a control section 350 (described below) generates a control signal when the user has operated the external I/F section 500, and the objective lens 230 changes the magnification based on the control signal.

The control device 300 includes the A/D conversion section 310, an image acquisition section 320, a determination section 330, the aperture control section 340, the control section 350 (signal processing control section), and a dimmer section 360. The A/D conversion section 310 is connected to the image acquisition section 320. The image acquisition section 320 is connected to the determination section 330, the dimmer section 360, and the display section 400. The determination section 330 is connected to the aperture control section 340. The aperture control section 340 is connected to the variable aperture 240 and the dimmer section 360, and controls the variable aperture 240 and the dimmer section 360. The control section 350 is bidirectionally connected to the A/D conversion section 310, the image acquisition section 320, the determination section 330, the aperture control section 340, the display section 400, and the external I/F section 500, and controls the A/D conversion section 310, the image acquisition section 320, the determination section 330, the aperture control section 340, the display section 400, and the external I/F section 500. The dimmer section 360 is connected to the white light source 110, and controls the white light source 110.

The A/D conversion section 310 converts an analog signal output from the imaging element 250 into a digital signal, and outputs the digital signal to the image acquisition section 320.

The image acquisition section 320 performs image processing (e.g., interpolation process, white balance process, color conversion process, and grayscale conversion process) on the digital signal output from the AD conversion section 310 based on a control signal output from the control section 350 to acquire an image of the object. The image acquisition section 320 outputs the acquired image of the object to the determination section 330 and the display section 400.

The determination section 330 sets an observation area, and determines whether or not the observation area is in focus. Specifically, the determination section 330 divides the observation area into a plurality of segmented observation areas, determines whether or not each segmented observation area is in focus, and outputs the determination results to the aperture control section 340.

The aperture control section 340 controls the aperture value based on the determination results of the determination section 330. Specifically, the aperture control section 340 decreases the aperture value (i.e., opens up the aperture) when all of the segmented observation areas are in focus. The aperture control section 340 calculates a target depth of field that includes the observation area when at least one of the segmented observation areas is out of focus, and sets the depth of field to the target depth of field by adjusting the aperture value.

The control section 350 is connected to the A/D conversion section 310, the image acquisition section 320, the determination section 330, the aperture control section 340, the display section 400, and the external I/F section 500, and outputs a control signal that controls the A/D conversion section 310, the image acquisition section 320, the determination section 330, the aperture control section 340, the display section 400, and the external I/F section 500.

The dimmer section 360 controls the intensity of light emitted from the white light source 110 so that the average brightness of the image of the object acquired by the image acquisition section 320 is constant. The dimmer section 360 changes the light intensity control method corresponding to a change in the aperture value. Specifically, when the average brightness of the image of the object acquired at a given time differs from a reference value set in advance, the dimmer section 360 controls the intensity of light based on the difference between the average brightness of the image of the object and the reference value so that the average brightness of the image of the object becomes equal to the reference value when a given time has elapsed. The dimmer section 360 controls the intensity of light for a given time at a constant change rate. When the dimmer section 360 has detected that the aperture value output from the aperture control section 340 has changed, the dimmer section 360 controls the intensity of light so that the average brightness of the image of the object does not change across the change in the aperture value. Specifically, the dimmer section 360 changes the intensity of light by a factor of $1/\alpha^2$ when the effective diameter of the lens has changed by a factor of $\alpha$ due to a change in the aperture value. The dimmer section 360 then controls the intensity of light by the above method based on the difference between the average brightness and the reference value.

The display section 400 outputs the image of the object acquired by the image acquisition section 320 to an image display device (e.g., endoscope monitor).

The external I/F section 500 is an interface that allows the user to input information to the endoscope apparatus, for example. The external I/F section 500 includes a power supply switch (power supply ON/OFF switch), a shutter button (imaging operation start button), a mode (e.g., imaging mode) switch button, and the like.

2.2. Determination Section

Figure 2:
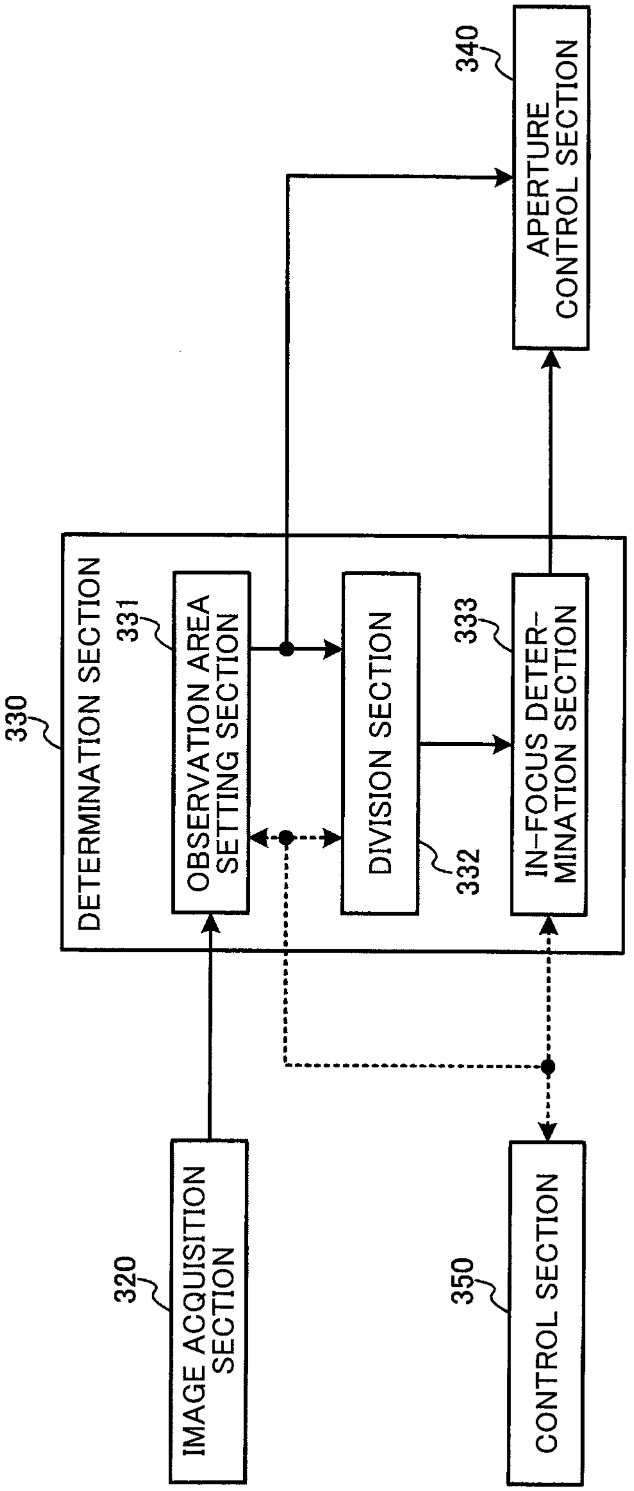
FIG. 2 shows a detailed configuration example of a determination section.

FIG. 2 shows a detailed configuration example of the determination section 330. As shown in FIG. 2, the determination section 330 includes an observation area setting section 331, a division section 332, and an in-focus determination section 333.

The image of the object acquired by the image acquisition section 320 is output to the observation area setting section 331. The observation area setting section 331 is connected to the division section 332 and the aperture control section 340. The division section 332 is connected to the in-focus determination section 333. The in-focus determination section 333 is connected to the aperture control section 340.

The observation area setting section 331 sets the observation area within the image of the object acquired by the image acquisition section 320 based on the pixel value of the image of the object. When the image of the object is a color image using an R signal, a G signal, and a B signal, for example, the observation area setting section 331 sets the observation area based on the R signal. This is because the R signal value reflects almost only the effects of distance. Specifically, each signal value is inversely proportional to the second power of the distance to the object. However, since the G signal and the B signal are affected by absorption by hemoglobin, the G signal value and the B signal value corresponding to a blood vessel decrease. Therefore, it is difficult to determine whether the G signal value and the B signal value are small due to a blood vessel or a long distance. On the other hand, the R signal is relatively rarely affected by absorption by hemoglobin, and its signal value reflects almost only the effects of distance. Therefore, the observation area can be set based on the distance to the object by utilizing the R signal.

Figure 3A:
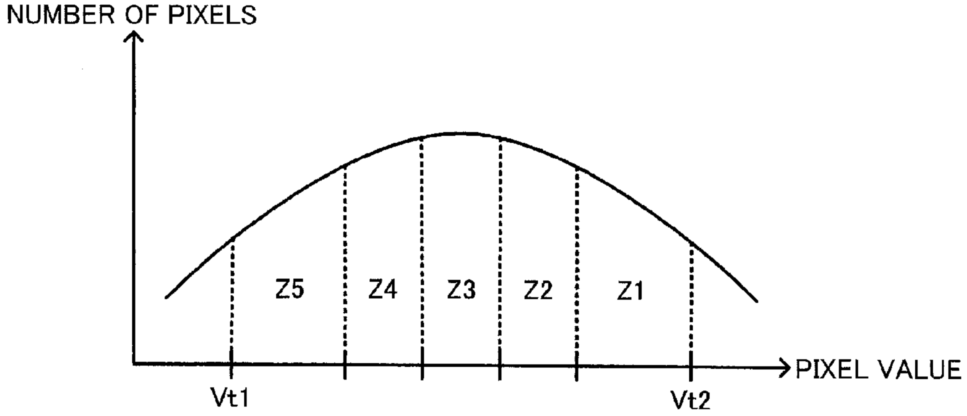
FIGS. 3A and 3B are views illustrative of a segmented observation area.
Figure 3B:
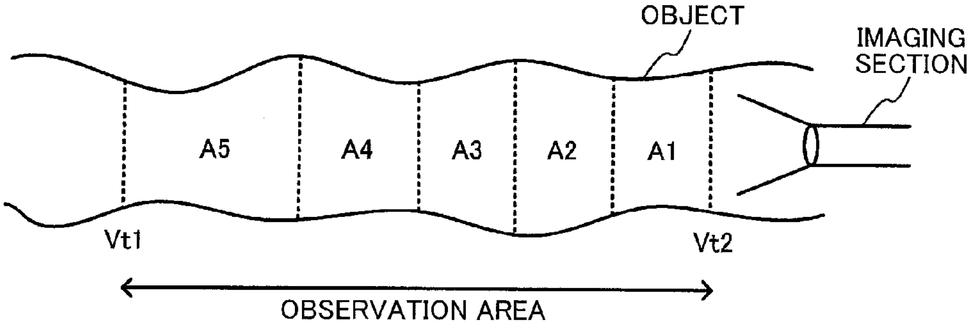

The observation area setting method is described in detail below. FIG. 3A schematically shows the histogram of the R signal value (pixel value). A first threshold value Vt1 and a second threshold value Vt2 larger than the first threshold value Vt1 are set, as shown in FIG. 3A. A pixel having an R signal value that is equal to or larger than the first threshold value Vt1 and is equal to or less than the second threshold value Vt2 is set to be a pixel that forms the observation area. This is because the R signal value of a distant object is small, and the R signal value of a close object is large. Specifically, the range from an object for which the R signal value is equal to the first threshold value Vt1 to an object for which the R signal value is equal to the second threshold value Vt2 is set to be the observation area (see FIG. 3B).

Note that a labeling process may be performed on the observation area by a known method, and an area in which the number of pixels to which an identical label is assigned is equal to or less than a given threshold value may be excluded from the observation area.

The first threshold value Vt1 and the second threshold value Vt2 are set based on the shape of the object. Specifically, when the object has a hollow tubular shape, the first threshold value Vt1 is set to a small value and the second threshold value is set to a large value as compared with the case where the object has another shape. The endoscope apparatus is configured so that the intensity of light applied to the object is controlled so that the average brightness of the image of the object is constant. Therefore, the endoscope apparatus determines that the intensity of light has been successfully controlled when the average brightness (e.g., the average R signal value) of the image of the object is within a given range, and sets the observation area by the above method. When the object has a hollow tubular shape, it is desired that a wide range from an object close to the end of the imaging section 200 to an object distant from the end of the imaging section 200 be in focus (i.e., deep focus). Therefore, the difference between the first threshold value Vt1 and the second threshold value Vt2 is increased so that such a wide range is set to be the observation area. When the object has a shape other than a hollow tubular shape, a wide range need not be in focus. Therefore, the difference between the first threshold value Vt1 and the second threshold value Vt2 is reduced as compared with the case where the object has a hollow tubular shape.

The first threshold value Vt1 and the second threshold value Vt2 are determined in advance from images obtained by capturing various objects (e.g., an object that has a hollow tubular shape). The shape of the object is determined from a statistical amount calculated from the histogram of the R signal value of the image of the object, for example. A kurtosis is used as the statistical amount, for example. The object is determined to have a hollow tubular shape when the kurtosis is equal to or larger than a given threshold value. When the object has a hollow tubular shape, since a range from a bright area that is close to the imaging section to a dark area that is distant from the imaging section is captured, the R signal value is distributed over a wide range, so that the histogram tends to broaden. Therefore, the shape of the object can be determined by utilizing the kurtosis that is a statistical amount that indicates the range of the histogram.

Although an example in which the observation area is set based on the R signal value of the image of the object, and the first threshold value Vt1 and the second threshold value Vt2 corresponding to the R signal value, has been described above, another configuration may also be employed. For example, the observation area may be set based on a luminance signal that is calculated from the RGB signal values by a known method, and a third threshold value and a fourth threshold value corresponding to the luminance signal.

The division section 332 divides the observation area set by the observation area setting section 331 into first to Nth segmented observation areas (N areas (N is a natural number)). Specifically, the division section 332 creates a histogram from the R signal value within the observation area, and divides the histogram into N sections (see FIG. 3A). In the example shown in FIG. 3A, the division section 332 divides the histogram into first to fifth sections Z1 to Z5. The division section 332 extracts pixels having an R signal value that is included within the respective sections Z1 to Z5 from the image of the object, and sets the pixels having an R signal value that is included within the respective sections Z1 to Z5 to be first to fifth segmented observation areas. The observation area is thus divided into first to fifth segmented observation areas A1 to A5 (see FIG. 3B). Since the R signal value is in inverse proportion to the square of distance, the segmented observation area corresponds to the distance from the imaging section.

For example, the division section 332 divides the histogram so that the number of pixels included in each section is as equal as possible. In the first embodiment, the average R signal value of each section is calculated, and the average value of the average R signal values of the respective sections is calculated as the average R signal value of the observation area. An in-focus determination process is performed on each section based on the average R signal value of the observation area. In this case, the average R signal value of the observation area can be appropriately calculated by causing the number of pixels included in each section to be equal.

Note that the observation area may be divided into N segmented observation areas by a known method (e.g., graph cutting method) other than the above method.

The in-focus determination section 333 determines whether or not each segmented observation area obtained by the division section 332 is in focus. Specifically, the in-focus determination section 333 calculates the contrast of each segmented observation area, determines that the segmented observation area is in focus when the contrast is equal to or larger than a given in-focus threshold value, and determines that the segmented observation area is out of focus when the contrast is smaller than the given in-focus threshold value.

For example, the contrast is calculated by performing a digital filtering process on the G signal or the B signal of each pixel included in the segmented observation area. The digital filtering process is performed on each signal. For example, the digital filtering process is performed using a Laplacian filter. The output value of the G signal or the B signal of each pixel included in the segmented observation area is obtained by the filtering process. The in-focus determination section 333 determines the absolute value of the output value to be the contrast. The in-focus determination section 333 determines whether or not each segmented observation area is in focus based on the result of a comparison between the contrast and the in-focus threshold value.

The in-focus threshold value is a value corresponding to the average R signal value calculated corresponding to each segmented observation area. Specifically, the in-focus determination section 333 refers to a table that stores the relationship between the average R signal value of each segmented observation area and the in-focus threshold value, and acquires the in-focus threshold value corresponding to the calculated average R signal value of each segmented observation area. The in-focus determination section 333 determines that the segmented observation area is in focus when the contrast of the segmented observation area is equal to or larger than the in-focus threshold value, and determines that the segmented observation area is out of focus when the contrast of the segmented observation area is smaller than the in-focus threshold value. The in-focus determination section 333 determines the calculated average R signal value of each segmented observation area to be a representative signal value, and outputs the representative signal value and the in-focus determination result for each segmented observation area to the aperture control section 340.

The digital filter used to calculate the contrast may be designed to analyze a spatial frequency from the G signal or the B signal of the image of the object acquired in advance, and enhance a frequency component characteristic of the image of the object.

2.3. Modification of Determination Section

Figure 4:
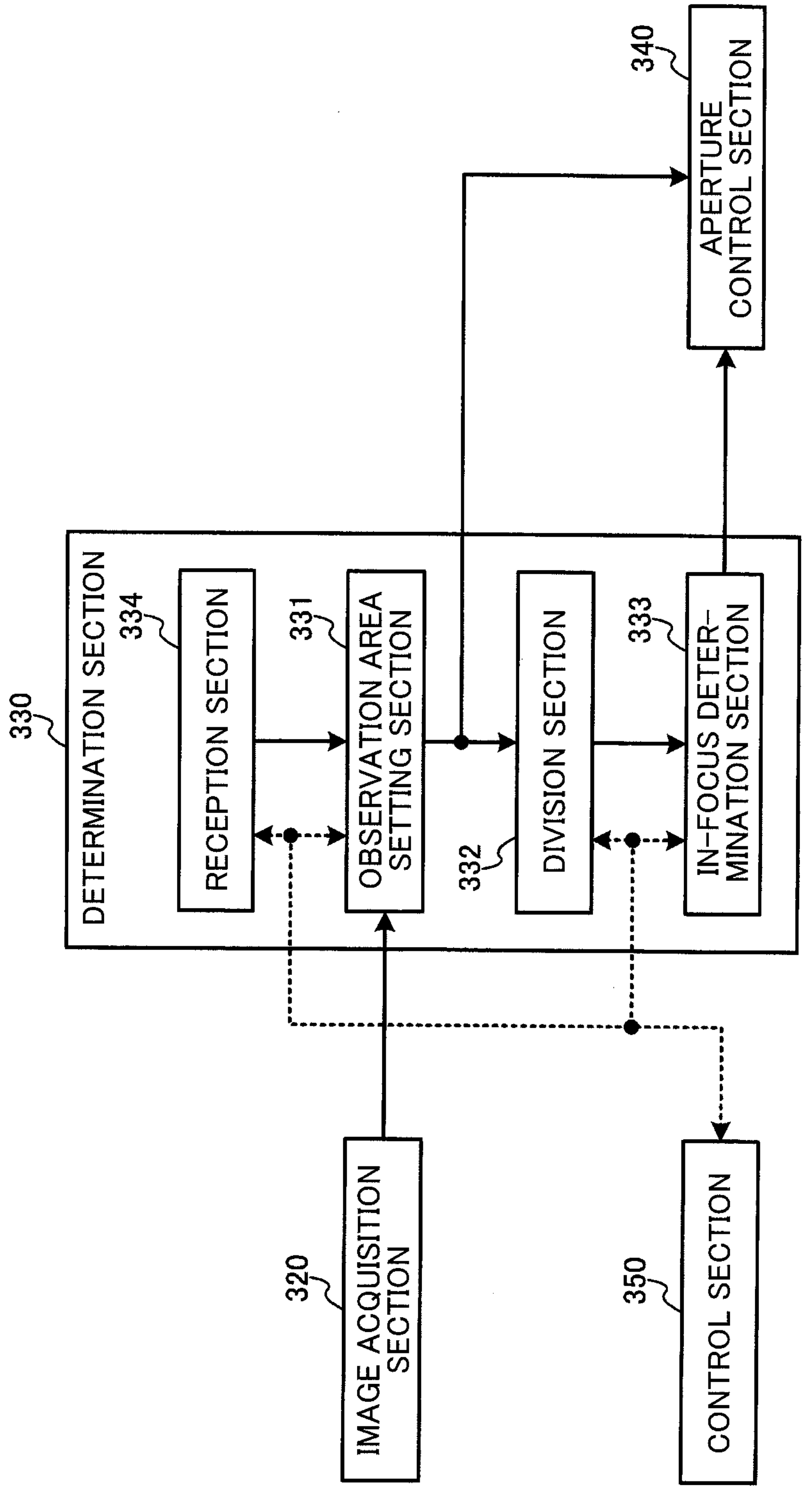
FIG. 4 shows a modification of a determination section.

FIG. 4 shows a modification of the determination section 330. As shown in FIG. 4, the determination section 330 includes the observation area setting section 331, the division section 332, the in-focus determination section 333, and a reception section 334. Note that the division section 332 and the in-focus determination section 333 are configured in the same manner as described above.

The reception section 334 receives information about the observation area input by the user as observation area auxiliary information, and outputs the observation area auxiliary information to the observation area setting section 331. Specifically, the observation area auxiliary information is input by the user through the external I/F section 500, and is output from the external I/F section 500 to the control section 350. The control section 350 generates a control signal that includes the observation area auxiliary information. The reception section 334 extracts the observation area auxiliary information from the control signal to receive the observation area auxiliary information.

The observation area auxiliary information includes the first threshold value Vt1 and the second threshold value Vt2, for example. In this case, the histogram of the image of the object is presented to the user, and the user inputs an arbitrary first threshold value Vt1 and an arbitrary second threshold value Vt2 based on the histogram using a keyboard or the like, for example.

Note that a combination of the first threshold value Vt1 and the second threshold value Vt2 corresponding to each object shape may be stored in advance, and the user may select the desired combination at an arbitrary timing. The observation area auxiliary information may be area information that indicates an area within the image of the object. In this case, the endoscope monitor includes a touch panel, and the user uses inputs area information on the image of the object displayed on the endoscope monitor using an input device (e.g., touch pen). The user may also input the area information by touching the touch panel.

The observation area setting section 331 sets the observation area within the image of the object by the method corresponding to the observation area auxiliary information output from the reception section 334. When the observation area auxiliary information includes the first threshold value Vt1 and the second threshold value Vt2, the observation area setting section 331 sets a pixel having an R signal value that is equal to or larger than the first threshold value Vt1 and is equal to or less than the second threshold value Vt2 to be a pixel that forms the observation area. When the observation area auxiliary information is the area information, the observation area setting section 331 sets the area indicated by the area information to be the observation area.

2.4. Aperture Control Section

The aperture control section 340 is described in detail below. The aperture control section 340 controls the aperture value of the variable aperture 240 based on the shape of the object determined by the observation area setting section 331, and a representative signal value and the in-focus determination result of each segmented observation area output from the in-focus determination section 333.

Figure 5:
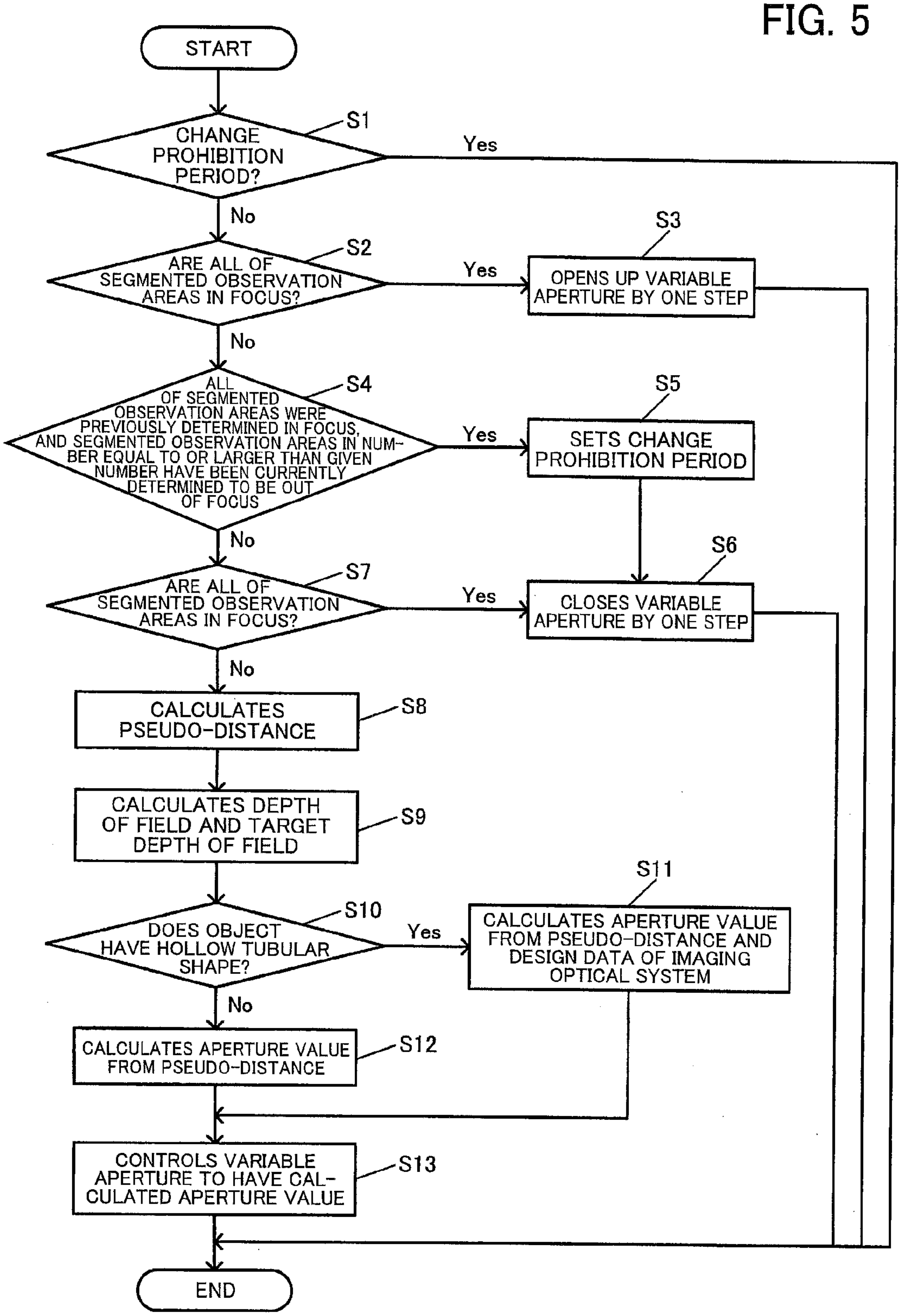
FIG. 5 shows an example of a flowchart of an aperture control process.

FIG. 5 shows an example of a flowchart of the aperture value control process (aperture control process) performed by the aperture control section 340. The aperture control section 340 performs the aperture control process each time the in-focus determination process has been performed. As shown in FIG. 5, the aperture control section 340 determines whether or not a change prohibition period has been set, the change prohibition period being a period in which a change in the aperture value is prohibited (step S1). The change prohibition period may be set by a process described later. The aperture control section 340 finishes the process when the change prohibition period has been set (step S1, Yes).

When the change prohibition period has not been set (step S1, No), the aperture control section 340 controls the aperture value based on the in-focus determination result. Specifically, the aperture control section 340 determines whether or not all of the segmented observation areas are in focus (step S2). When all of the segmented observation areas are in focus (step S2, Yes), the aperture control section 340 decreases the aperture value. For example, the aperture control section 340 opens up the variable aperture 240 by one step (step S3).

When at least one of the segmented observation areas is out of focus (step S2, No), the aperture control section 340 determines whether or not the step S3 was performed during the preceding aperture control process, and determines the number of segmented observation areas that have been determined to be out of focus (step S4). Note that the preceding aperture control process refers to the aperture control process that was performed corresponding to the latest in-focus determination process excluding the in-focus determination process that corresponds to the current aperture control process. When the step S3 was performed during the preceding aperture control process, and the number of segmented observation areas that have been determined to be out of focus is equal to or larger than a given number (step S4, Yes), the aperture control section 340 sets the change prohibition period (step S5), and restores the aperture value of the variable aperture 240 (step S6). The depth of field can be stabilized when the user observes the object in a deep-focus state by thus controlling the aperture value.

When the step S3 was not performed during the preceding aperture control process, and the number of segmented observation areas that have been determined to be out of focus is smaller than the given number (step S4, No), the aperture control section 340 determines whether or not all of the segmented observation areas are out of focus (step S7). When all of the segmented observation areas are out of focus (step S7, Yes), the aperture control section 340 increases the aperture value. For example, the aperture control section 340 closes the variable aperture 240 by one step (step S6).

When at least one of the segmented observation areas is in focus (step S7, No), the aperture control section 340 calculates a pseudo-distance from the end of the imaging section to the object (step S8). Specifically, the aperture control section 340 calculates the reciprocal of the square root of the representative signal value as the pseudo-distance. The aperture control section 340 then calculates the depth of field at the current aperture value and the target depth of field at the target aperture value based on the pseudo-distance (step S9).

Figure 6:
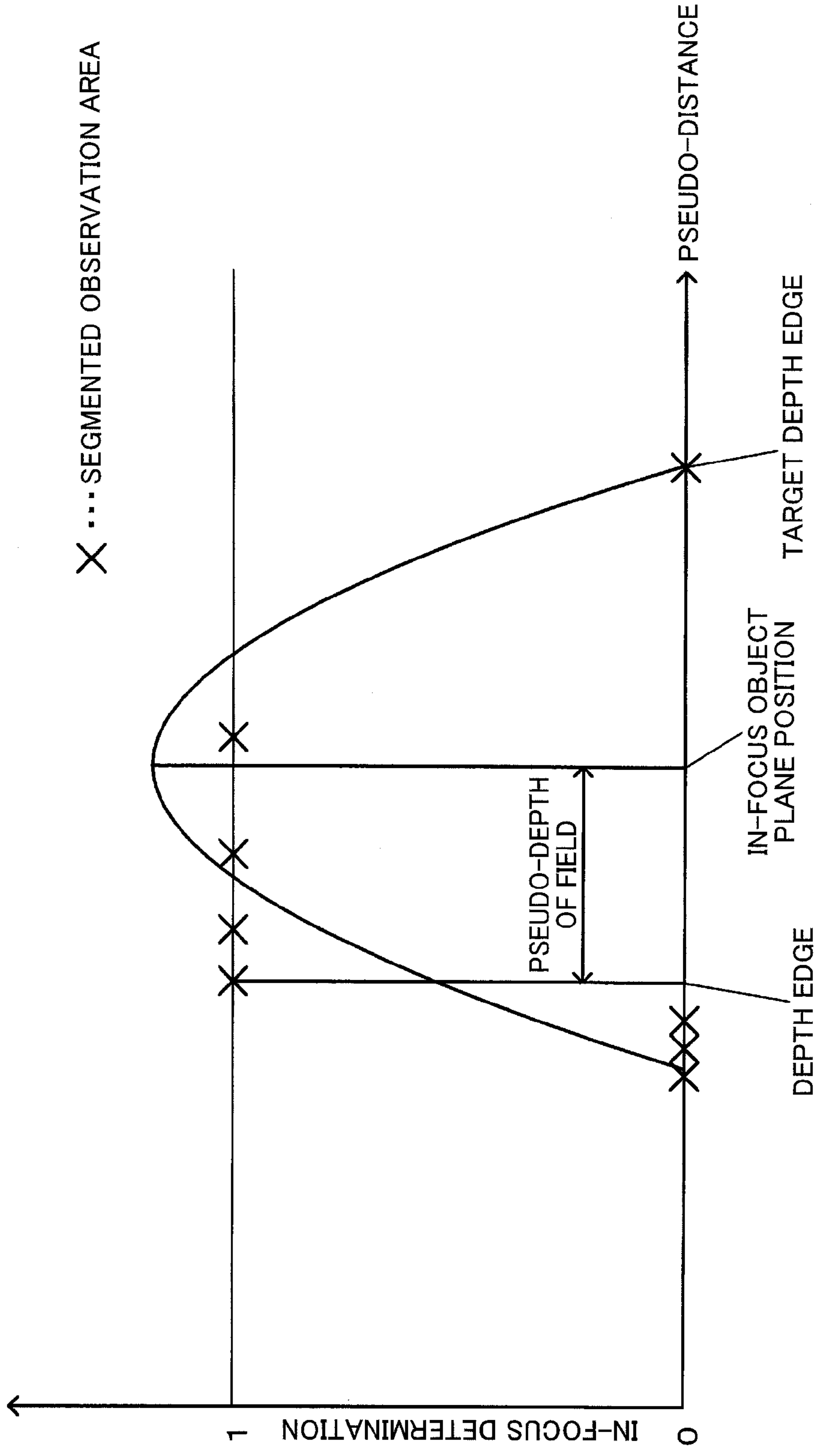
FIG. 6 is a view illustrative of calculation of an aperture value during an aperture control process.

Specifically, the aperture control section 340 generates a graph in which the horizontal axis indicates the pseudo-distance and the vertical axis indicates the in-focus determination result (see FIG. 6). Note that a case where the segmented observation area is determined to be in focus is indicated by "1", and a case where the segmented observation area is determined to be out of focus is indicated by "0". The aperture control section 340 then calculates an upward quadratic approximate function by the least-square method using the plotted points. The aperture control section 340 determines the pseudo-distance corresponding to the position of the vertex of the approximate function to be the in-focus object plane position of the imaging optical system of the endoscope apparatus. Note that the in-focus object plane position, the depth of field, and the target depth of field are indicated by the pseudo-distance instead of the actual physical distance. The aperture control section 340 determines the position of the segmented observation area that has been determined to be in focus and is farthest from the in-focus object plane position along the horizontal axis to be the depth edge. The aperture control section 340 determines the pseudo-distance from the in-focus object plane position to the depth edge to be a pseudo-depth of field.

When only one segmented observation area has been determined to be in focus (see FIG. 7), the aperture control section 340 determines the pseudo-distance corresponding to the position of the segmented observation area that has been determined to be in focus to be the in-focus object plane position. The aperture control section 340 determines an intermediate position (e.g., middle position) between the position of the segmented observation area that is nearest to the in-focus object plane position along the horizontal axis and the in-focus object plane position to be the depth edge. The aperture control section 340 determines the pseudo-distance from the in-focus object plane position to the depth edge to be the pseudo-depth of field.

Although an example in which the relationship between the pseudo-distance and the in-focus determination result may be approximated by a quadratic function has been described above, the relationship between the pseudo-distance and the in-focus determination result is approximated by a Gaussian function. In this case, the average value of the Gaussian function is determined to be the in-focus object plane position, and the standard deviation of the Gaussian function is determined to be the pseudo-depth of field. The position of the segmented observation area that has been determined to be in focus and has the smallest Gaussian approximation function value is determined to be the depth edge.

The aperture control section 340 then determines whether the pseudo-depth of field is the back depth of field or the front depth of field based on the positional relationship between the depth edge and the in-focus object plane position (see FIG. 6). Specifically, the aperture control section 340 determines that the pseudo-depth of field is the back depth of field when the depth edge is farther than the in-focus object plane position, and determines that the pseudo-depth of field is the front depth of field when the depth edge is nearer than the in-focus object plane position. The aperture control section 340 determines the segmented observation area that is farthest from the in-focus object plane position to be the target depth edge, and determines the pseudo-distance between the target depth edge and the in-focus object plane position to be the target depth of field. The aperture control section 340 determines the target depth of field to be the back target depth of field when the target depth edge is farther than the in-focus object plane position, and determines the target depth of field to be the front target depth of field when the target depth edge is nearer than the in-focus object plane position.

The aperture control section 340 then determines the shape of the object (step S10) (see FIG. 5). When the object has a hollow tubular shape (step S10, Yes), the aperture control section 340 calculates the target aperture value based on the value calculated based on the pseudo-distance and the design data of the imaging optical system of the endoscope apparatus (step S11).

The aperture value calculation process is described in detail below. The depth of field is described below. The back depth of field $K_b$ and the front depth of field $K_f$ are respectively calculated by the following expressions (1) and (2). Note that L is the in-focus object plane position (distance), r is the diameter of the permissible circle of confusion, F is the F-number, and f is the focal length.

$$K_b = \frac{r \times F \times L^2}{f^2 - r \times F \times L} \tag{1}$$

$$K_f = \frac{r \times F \times L^2}{f^2 + r \times F \times L} \tag{2}$$

The F-number is calculated by the following expression (3). Note that d is the effective diameter of the lens at the current aperture value. The effective diameter d decreases as the aperture value increases.

$$F = \frac{f}{d} \tag{3}$$

The expressions (1) and (2) can be respectively rewritten into the following expressions (4) and (5).

$$K_b = \frac{r \times \left(\frac{1}{d}\right) \times L^2}{f - r \times \left(\frac{1}{d}\right) \times L} \tag{4}$$

$$K_f = \frac{r \times \left(\frac{1}{d}\right) \times L^2}{f + r \times \left(\frac{1}{d}\right) \times L} \tag{5}$$

The back target depth of field $O_b$ and the front target depth of field $O_f$ are respectively calculated by the following expressions (6) and (7). Note that d' is the target effective diameter of the lens.

$$O_b = \frac{r \times \left(\frac{1}{d'}\right) \times L^2}{f - r \times \left(\frac{1}{d'}\right) \times L} \tag{6}$$

$$O_f = \frac{r \times \left(\frac{1}{d'}\right) \times L^2}{f + r \times \left(\frac{1}{d'}\right) \times L} \tag{7}$$

Figure 8:
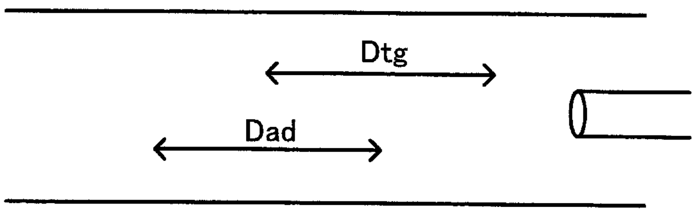
FIG. 8 is a view illustrative of an aperture control process when the object has a hollow tubular shape.

The target effective diameter d' of the lens is calculated as described below. When the target effective diameter d' has been calculated, the F-number can be calculated by F=f/d'. When the object has a hollow tubular shape (see FIG. 8), whether or not the object is in focus within a given constant range Dad relative to the end of the endoscope is determined. Specifically, since the imaging section can be inserted into and removed from the object having a hollow tubular shape, the observation area can be positioned within the depth of field by moving the imaging section when the depth of field Dad is provided. In this case, since it suffices that the depth of field Dad be equal to the target depth of field Dtg, the target effective diameter d' is calculated by the following expressions (8) and (9). The target effective diameter d' (expression (9)) is calculated by substituting $L=L_t$, $r=r_t$, and $f=f_t$ into the expressions (6) and (7), and calculating $O_b+O_f=W_o$ for the target effective diameter d'. Note that the depth of field Dad may be equal to or greater than the target depth of field Dtg.

$$W_o = \frac{O_b + O_f}{K_b + K_f} \times W_t \tag{8}$$

$$d' = \frac{r_t L_t^2 \left(1 + 2\sqrt{1 + \left(\frac{W_o}{L_t}\right)^2}\right)}{f_t W_o} \tag{9}$$

where, $W_t$ is the actual physical depth of field, $L_t$ is the actual physical in-focus object plane position (distance), $R_t$ is the actual physical diameter of the permissible circle of confusion, and $f_t$ is the actual physical focal length. These values are known or calculated from the design data of the imaging optical system of the endoscope apparatus.

Figure 7:
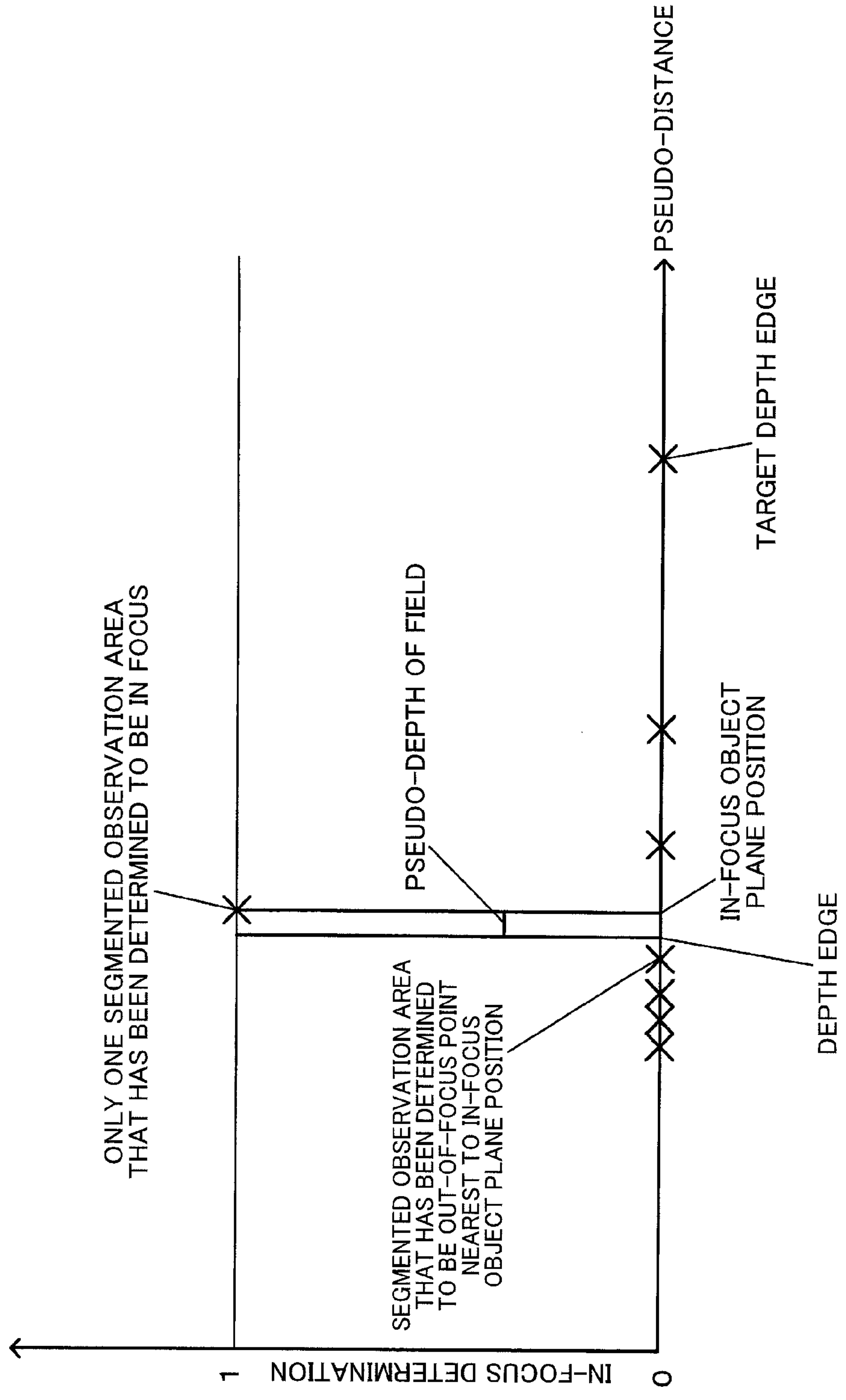
FIG. 7 is a view illustrative of calculation of an aperture value during an aperture control process.

In FIGS. 6 and 7, one of the back depth of field $K_b$ and the front depth of field $K_f$, and one of the back target depth of field $O_b$ and the front target depth of field $O_f$ are calculated. $W_o$ (expression (8)) is calculated on the assumption that $K_b=K_f$ and $O_b=O_f$. Alternatively, the pseudo-distance from the farthest position to the nearest position of the segmented observation areas that have been determined to be in focus may be determined to be $K_b+K_f$, and the pseudo-distance from the farthest position to the nearest position of the segmented observation areas may be determined to be $O_b+O_f$.

Figure 9:
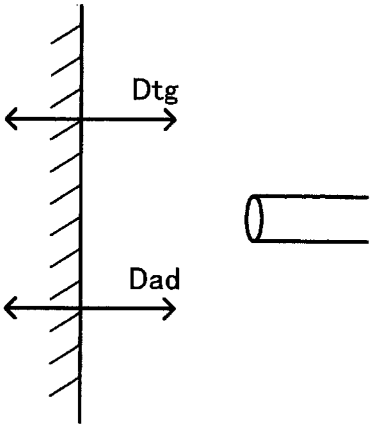
FIG. 9 is a view illustrative of an aperture control process when the object does not have a hollow tubular shape.

When the object does not have a hollow tubular shape (step S10, No), the aperture control section 340 calculates the target aperture value from a value calculated based on the pseudo-distance (step S12) (see FIG. 5). When the object does not have a hollow tubular shape (see FIG. 9), whether or not the entire object positioned at a given position is in focus is determined. Specifically, it suffices that the depth of field Dad coincide with the target depth of field Dtg (i.e., the depth edge coincide with the target depth edge).

When the depth edge is farther than the in-focus object plane position, and the target depth edge is farther than the in-focus object plane position, the target effective diameter d' of the lens is calculated by the following expression (10). In this case, the target effective diameter d' (expression (10)) is calculated based on the expressions (4) and (6).

$$d' = \frac{(L+O_b)K_b}{(L+K_b)O_b} \times d \quad (10)$$

When the depth edge is farther than the in-focus object plane position, and the target depth edge is nearer than the in-focus object plane position, the target effective diameter d' of the lens is calculated by the following expression (11). In this case, the target effective diameter d' (expression (11)) is calculated based on the expressions (4) and (7).

$$d' = \frac{(L-O_f)K_b}{(L+K_b)O_f} \times d \quad (11)$$

When the depth edge is nearer than the in-focus object plane position, and the target depth edge is farther than the in-focus object plane position, the target effective diameter d' of the lens is calculated by the following expression (12). In this case, the target effective diameter d' (expression (12)) is calculated based on the expressions (5) and (6).

$$d' = \frac{(L+O_b)K_f}{(L-K_f)O_b} \times d \quad (12)$$

When the depth edge is nearer than the in-focus object plane position, and the target depth edge is nearer than the in-focus object plane position, the target effective diameter d' of the lens is calculated by the following expression (13). In this case, the target effective diameter d' (expression (13)) is calculated based on the expressions (5) and (7).

$$d' = \frac{(L-O_f)K_f}{(L-K_f)O_f} \times d \quad (13)$$

The aperture control section 340 then outputs the aperture control signal to the variable aperture 240 so that the effective diameter d' of the lens is calculated by one of the expressions (8) to (13) to control the aperture value of the variable aperture 240 (step S13) (see FIG. 5). The aperture control section 340 finishes the aperture control process when the step S3, S6, or S13 has ended.

When the aperture control section 340 has detected that a magnification operation of the objective lens 230 has started based on the control signal output from the control section 350, the aperture control section 340 sets the aperture value of the variable aperture 240 to a given aperture value that corresponds to the magnification operation. For example, when performing a magnifying observation operation on the object, the depth of field decreases as compared with the case of performing a normal observation operation on the object, so that the object may be easily out of focus due to a shake in the optical axis direction. Therefore, an aperture value that implements a depth of field that encompasses the object even if a shake in the optical axis direction or the like occurs to a certain extent is acquired in advance. The aperture value is acquired corresponding to each magnification of the objective lens 230.

According to the first embodiment, the control device 300 includes the image acquisition section 320, the determination section 330, and the aperture control section 340. The image acquisition section 320 acquires an image of the object captured by the imaging optical system of the endoscope apparatus. The determination section 330 determines whether or not the observation area is in focus based on the pixel value of each pixel within the image of the object, the observation area being an observation target area within the image of the object. The aperture control section 340 controls the aperture of the imaging optical system based on the result of the determination.

This makes it possible to determine whether or not the object within the observation target range for the user is in focus based on the image of the object, and bring the observation target range into focus by controlling the variable aperture of the imaging optical system when the object within the observation target range is out of focus. Therefore, an image in which the observation target range is in focus can be presented to the user. Moreover, since the aperture value can be controlled so that a minimum necessary range is brought into focus, a decrease in resolution due to a small aperture blur can be minimized. Since it is unnecessary to reduce the frame rate, differing from JP-A-2009-240531, the user does not become so tired during observation.

In the first embodiment, the imaging optical system corresponds to the objective lens 230, the variable aperture 240, and the imaging element 250 shown in FIG. 1. The aperture corresponds to the variable aperture 240. The term "observation area" used herein refers to an area within the image of the object that is observed by the user. The observation area may be set by the observation area setting section 331, or may be set based on an instruction issued by the user, for example. The observation area may be a single area, or may be divided into a plurality of segmented observation areas.

As shown in FIG. 2, the determination section 330 includes a division section 332 that divides the observation area into a plurality of segmented observation areas. The determination section 330 determines whether or not each segmented observation area is in focus. The aperture control section 340 controls the aperture of the imaging optical system based on the result of the determination on each segmented observation area.

Specifically, the aperture control section 340 decreases the aperture value of the aperture when the determination section 330 has determined that all of the segmented observation areas are in focus (S2 and S3 in FIG. 5). The aperture control section 340 increases the aperture value of the aperture when the determination section 330 has determined that at least one of the segmented observation areas is out of focus (S4 to S13 in FIG. 5).

According to this configuration, the depth of field is reduced when all of the segmented observation areas are in focus, and is increased when at least one of the segmented observation areas is out of focus. This makes it possible to implement a minimum necessary depth of field that encompasses the observation area.

Note that the term "aperture value" refers to a value (e.g., F-number) that indicates the area of the aperture. The area of the aperture increases when decreasing the aperture value, and decreases when increasing the aperture value. The aperture value may be set so that the aperture value can be adjusted either non-stepwise or stepwise.

The aperture control section 340 controls the aperture of the imaging optical system so that corresponding points in real space that respectively correspond to the segmented observation areas are included within the depth of field of the imaging optical system when the determination section 330 has determined that at least one of the segmented observation areas is out of focus (S8 to S10, S12, and S13 in FIG. 5). For example, the aperture control section 340 performs the above aperture control when it has been determined that the object does not have a hollow tubular shape.

This makes it possible to calculate an aperture value at which the corresponding points in real space that respectively correspond to the segmented observation areas are included within the depth of field, and control the aperture of the imaging optical system based on the calculated aperture value. This makes it possible to implement a minimum necessary depth of field that encompasses the observation area.

Note that the corresponding points in real space that respectively correspond to the segmented observation areas refer to points on the optical axis that correspond to the representative distance from the imaging section to each segmented observation area, for example. When the average R signal value of the segmented observation area is determined to be the representative signal value, for example, the pseudo-distance that is the reciprocal of the square root of the representative signal value corresponds to the representative distance. In a second embodiment described later, the actual distance from the imaging section to each segmented observation area estimated by a distance estimation section 370 corresponds to the representative distance.

In the first embodiment, the aperture control section 340 controls the aperture of the imaging optical system so that at least the farthest point and the nearest point (target depth edge) among the corresponding points in real space that respectively correspond to the segmented observation areas are included within the depth of field of the imaging optical system (see FIG. 6, for example). More specifically, the aperture control section 340 controls the aperture of the imaging optical system so that the farthest point coincides with the far point of the depth of field (i.e., the back target depth of field coincides with the back depth of field), or the nearest point coincides with the near point of the depth of field (i.e., the front target depth of field coincides with the front depth of field) (see the expressions (10) to (13)).

This makes it possible to implement a minimum necessary depth of field that encompasses the observation area by controlling the aperture value so that the corresponding points in real space that respectively correspond to the segmented observation areas are included within the depth of field.

The aperture control section 340 controls the aperture of the imaging optical system so that the depth of field of the imaging optical system is equal to or greater than the distance between the nearest point and the farthest point among the corresponding points in real space that respectively correspond to the segmented observation areas when the determination section 330 has determined that at least one of the segmented observation areas is out of focus (S8 to S11 and S13 in FIG. 5). For example, the aperture control section 340 performs the above aperture control when it has been determined that the object has a hollow tubular shape.

This makes it possible to calculate an aperture value at which the depth of field is equal to or greater than the target depth of field, and control the aperture of the imaging optical system based on the calculated aperture value. This makes it possible to provide a depth of field required to bring the observation area into focus (see FIG. 8, for example).

The aperture control section 340 sets the change prohibition period in which a change in the aperture value is prohibited when the determination section 330 has previously determined that all of the segmented observation areas are in focus, and has currently determined that segmented observation areas among the segmented observation areas in a number equal to or larger than a given number are out of focus (S4, S5, and S1 in FIG. 5). The aperture control section 340 does not change the aperture value until the change prohibition period elapses.

This makes it possible to suppress a situation in which a rapid change in the depth of field repeatedly occurs. Specifically, when reducing the depth of field by opening up the aperture (see S2 and S3 in FIG. 5), the depth of field may change to a large extent when adjusting the aperture value by one step. In this case, if the depth of field is restored by closing the aperture value by one step (i.e., the depth of field is repeatedly changed), an image inconvenient to the user may be obtained. According to the first embodiment, a rapid change in the depth of field can be suppressed by providing the change prohibition period.

The aperture control section 340 increases the aperture value of the aperture of the imaging optical system when the determination section 330 has determined that the observation area is out of focus.

The observation area may be divided into a plurality of segmented observation areas, or may be a single area. When the observation area is a single area, the aperture value may be decreased (i.e., the aperture may be opened up) by one step when the observation area has been determined to be in focus, and may be increased (i.e., the aperture may be closed) by one step when the observation area has been determined to be out of focus, for example.

As shown in FIG. 2, the determination section 330 includes the observation area setting section 331 that sets the observation area within the image of the object. The determination section 330 determines whether or not the observation area is in focus based on the pixel value (e.g., average R signal value) of each pixel within the observation area. Specifically, the observation area setting section 331 sets the observation area based on the pixel value (R signal value) of each pixel within the image of the object.

This makes it possible to automatically set the observation area using the observation area setting section 331, and determine whether or not the observation area is in focus.

As shown in FIG. 4, the determination section 330 may further include the reception section 334 that receives information (observation area auxiliary information) that specifies the observation area within the image of the object from the user. In this case, the observation area setting section 331 sets the observation area based on the received information.

This makes it possible to set the area indicated by the user to be the observation area, and determine whether or not the observation area is in focus. The information that specifies the observation area may be the threshold values Vt1 and Vt2, coordinate information that indicates an area, or the like.

The image of the object may be a color image that has an R channel, a G channel, and a B channel. The determination section 330 may include a contrast calculation section that calculates the contrast of at least one of the G channel and the B channel. The determination section 330 may determine whether or not the observation area is in focus based on the calculated contrast.

This makes it possible to determine whether or not the observation area is in focus based on the contrast of the G channel or the B channel. It is also possible to determine whether or not the observation area is in focus based on the contrast of the G channel and the contrast of the B channel. Since the blood vessel structure is easily determined by absorption by hemoglobin when using the G channel or the B channel, the accuracy of the in-focus determination process using the contrast can be improved. Note that the contrast calculation section corresponds to the in-focus determination section 333 shown in FIGS. 2 and 4.

The imaging optical system may be configured so that the imaging magnification of the object can be variably set (i.e., may have a magnification function that magnifies part of the object). The aperture control section 340 may control the aperture value of the aperture corresponding to the imaging magnification. Specifically, the aperture control section 340 may control the aperture value based on the in-focus object plane distance or the in-focus object plane position of the imaging optical system that has changed corresponding to the imaging magnification so that the imaging optical system has a given depth of field.

This makes it possible to suppress a situation in which the observation area is not encompassed within the depth of field due to a shake in the optical axis direction.

The imaging magnification of the imaging optical system can be variably set by moving the end of the imaging section closer to the object and moving the in-focus object plane position closer to the imaging section, for example. In this case, the aperture value is controlled corresponding to the in-focus object plane position. It is also possible to variably set the imaging magnification of the imaging optical system by increasing the focal length of the imaging optical system via an optical zoom. In this case, the aperture value is controlled corresponding to the focal length.

As shown in FIG. 1, the control device further includes the dimmer section 360 that controls the intensity of light applied to the object. The dimmer section 360 controls the intensity of light based on the aperture value of the aperture.

This makes it possible to suppress a situation in which the brightness of the image changes due to a change in the aperture value. For example, the average brightness of the image can be kept constant by controlling the intensity of light so that the average brightness (e.g., luminance) of the image is identical across a change in the aperture value.

3. Second Embodiment

In the second embodiment, deep focus is implemented while further suppressing a decrease in resolution by controlling the in-focus object plane position in addition to the aperture value. The details thereof are described below.

Figure 10:
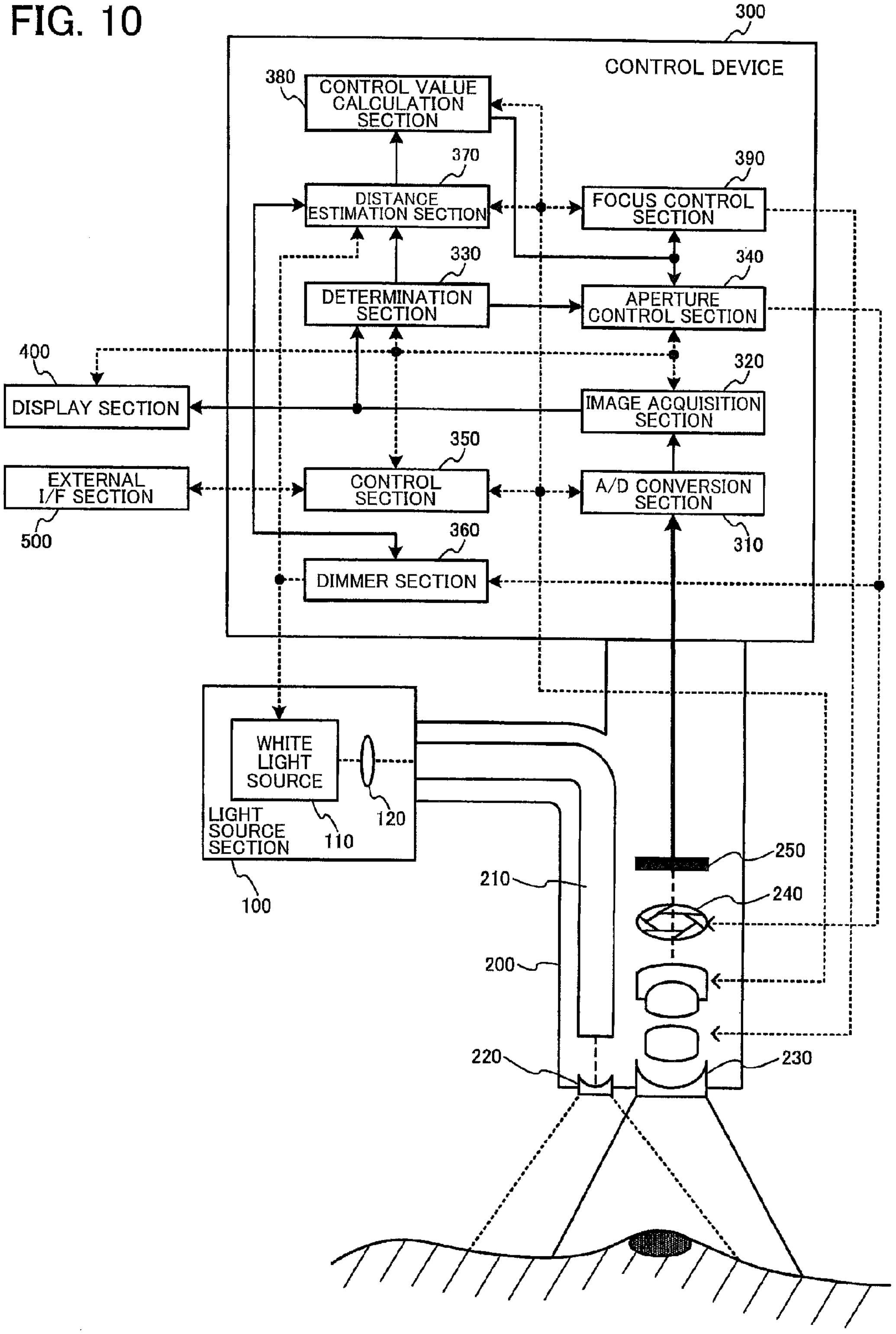
FIG. 10 shows a second configuration example of an endoscope apparatus according to one embodiment of the invention.

FIG. 10 shows a configuration example of an endoscope apparatus according to the second embodiment. The endoscope apparatus includes a light source section 100, an imaging section 200, a control device 300, a display section 400, and an external I/F section 500. Note that the elements other than the imaging section 200 and the control device 300 are the same as those described above in connection with the first embodiment. Therefore, description of these elements is appropriately omitted.

The imaging section 200 includes a light guide fiber 210, an illumination lens 220, an objective lens 230, a variable aperture 240, and an imaging element 250. The elements other than the objective lens 230 are the same as those described above in connection with the first embodiment.

The objective lens 230 further has a in-focus object plane position adjustment function. The in-focus object plane position is adjusted based on a in-focus object plane position control signal output from a focus control section 390 (described below).

The control device 300 includes an A/D conversion section 310, an image acquisition section 320, a determination section 330, an aperture control section 340, a control section 350, a dimmer section 360, the distance estimation section 370, a control value calculation section 380, and the focus control section 390. The A/D conversion section 310, the image acquisition section 320, the control section 350, and the dimmer section 360 are the same as those described above in connection with the first embodiment.

The determination section 330 is connected to the aperture control section 340 and the distance estimation section 370. The aperture control section 340 is connected to the variable aperture 240 and the dimmer section 360, and controls the variable aperture 240 and the dimmer section 360. The dimmer section 360 is connected to the white light source 110 and the distance estimation section 370. The distance estimation section 370 is connected to the control value calculation section 380. The control value calculation section 380 is connected to the aperture control section 340 and the focus control section 390. The focus control section 390 is connected to the objective lens 230, and controls the in-focus object plane position.

Figure 11:
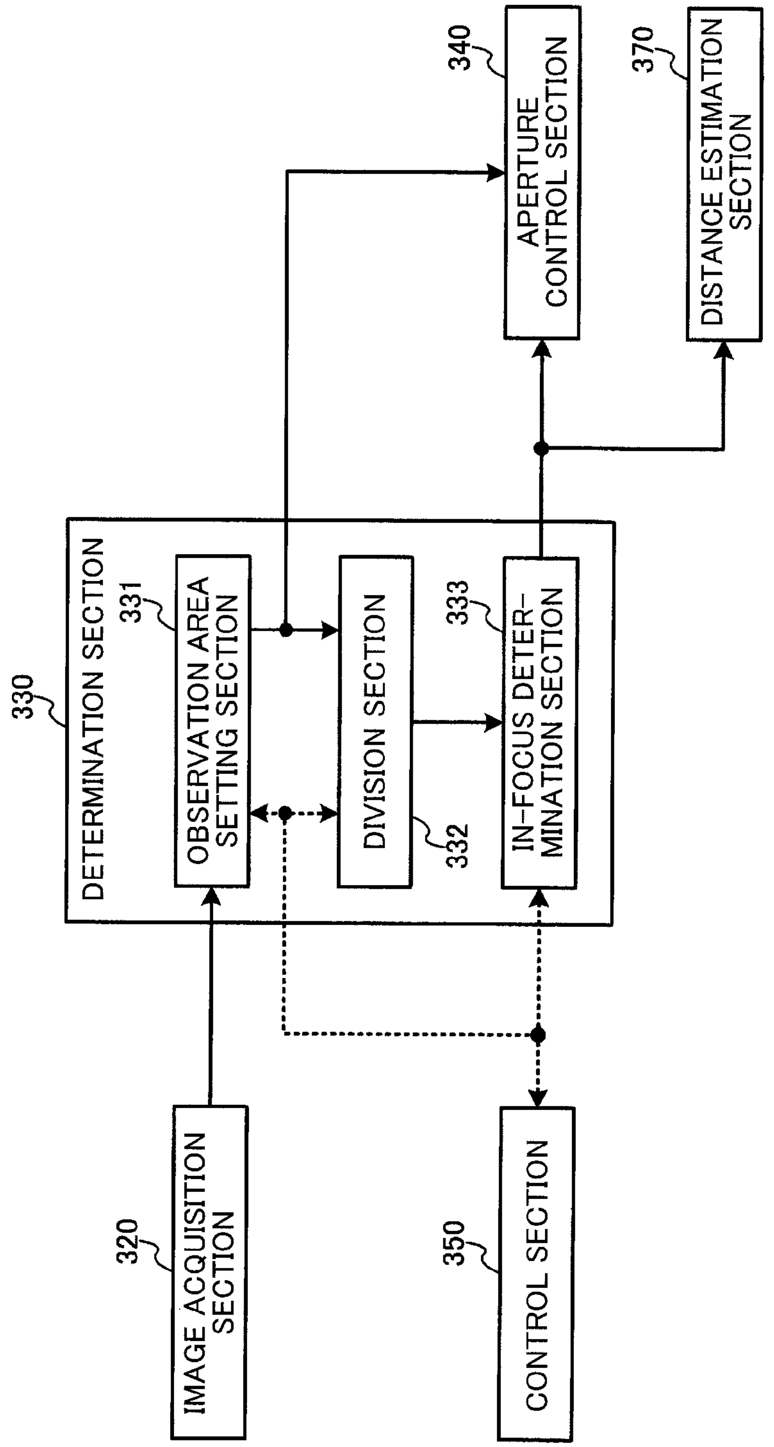
FIG. 11 shows a second detailed configuration example of a determination section.

FIG. 11 shows a second detailed configuration example of the determination section 330. As shown in FIG. 11, the determination section 330 includes an observation area setting section 331, a division section 332, and an in-focus determination section 333. The elements other than the in-focus determination section 333 are the same as those described above in connection with the first embodiment.

The in-focus determination section 333 determines whether or not each segmented observation area is in focus in the same manner as in the first embodiment. The in-focus determination section 333 outputs the in-focus determination result to the aperture control section 340 and the distance estimation section 370.

The dimmer section 360 shown in FIG. 10 controls the intensity of light emitted from the white light source 110 so that the average brightness of the image of the object acquired by the image acquisition section 320 is constant in the same manner as in the first embodiment. The dimmer section 360 changes the light intensity control method corresponding to a change in the aperture value. The dimmer section 360 notifies the distance estimation section 370 of the intensity of light emitted from the white light source 110.

The distance estimation section 370 estimates the physical distance to the object corresponding to the segmented observation area based on the pixel value of the segmented observation area and the in-focus determination process result for the segmented observation area output from the determination section 330, and the intensity of light emitted from the white light source 110 notified by the dimmer section 360. When the determination section 330 has determined that all of the segmented observation areas are in focus, the distance estimation section 370 does not estimate the physical distance to the object. When the determination section 330 has determined that at least one of the segmented observation areas is out of focus, the distance estimation section 370 estimates the physical distance to the object. Specifically, an image of the object is acquired while changing the distance and the intensity of light emitted from the white light source 110, and the pixel value (e.g., R signal value) of the image of the object corresponding to each intensity of light and each distance is stored in a table. The distance estimation section 370 refers to the table based on the intensity of light notified by the dimmer section 360 and the representative signal value of each segmented observation area output from the determination section 330, and estimates the object distance corresponding to each segmented observation area.

The distance estimation section 370 determines the segmented observation area that is farthest from the imaging section to be the farthest point, and determines the segmented observation area that is nearest to the imaging section to be the nearest point. The distance estimation section 370 outputs a farthest point distance that is the object distance at the farthest point and a nearest point distance that is the object distance at the nearest point to the control value calculation section 380.

Note that the object distance Dt may be estimated by the following expression (14) based on the relationship between the depth of field calculated at the pseudo-distance and the physical depth of field calculated based on the design data of the imaging optical system, in the same manner as the aperture control section 340 according to the first embodiment. Note that $W_t$ is the physical depth of field calculated based on the design data of the imaging optical system, $W_p$ is the depth of field calculated at the pseudo-distance, and Dp is the pseudo-distance to the object.

$$D_t = \frac{W_t}{W_p} \times D_p \tag{14}$$

The control value calculation section 380 calculates the aperture value and the in-focus object plane position based on the farthest point distance and the nearest point distance output from the distance estimation section 370. Specifically, the control value calculation section 380 calculates an aperture value and a in-focus object plane position at which the farthest point coincides with the far point of the depth of field of the imaging optical system, and the nearest point coincides with the near point of the depth of field of the imaging optical system.

The aperture value/in-focus object plane position calculation process is described in detail below. The distance $D_b$ to the far point of the depth of field and the distance $D_f$ to the near point of the depth of field are respectively calculated by the following expressions (15) and (16). Note that L is the in-focus object plane position (distance), r is the diameter of the permissible circle of confusion, F is the F-number, and f is the focal length.

$$D_b = L + \frac{r \times F \times L^2}{f^2 - r \times F \times L} \tag{15}$$

$$D_f = L - \frac{r \times F \times L^2}{f^2 + r \times F \times L} \tag{16}$$

The expressions (15) and (16) can be respectively rewritten into the following expressions (17) and (18).

$$D_b = L + \frac{r \times \left(\frac{1}{d}\right) \times L^2}{f - r \times \left(\frac{1}{d}\right) \times L} \tag{17}$$

$$D_f = L - \frac{r \times \left(\frac{1}{d}\right) \times L^2}{f + r \times \left(\frac{1}{d}\right) \times L} \tag{18}$$

Solving the expressions (17) and (18) for L and d yields the following expressions (19) and (20). r and f are calculated from the design data of the imaging optical system.

$$L = \frac{2D_b D_f}{D_b + D_f} \tag{19}$$

$$d = \frac{2D_b D_f}{D_b - D_f}\frac{r}{f} \tag{20}$$

According to the second embodiment, the farthest point and the far point of the depth of field are caused to coincide with each other, and the nearest point and the near point of the depth of field are caused to coincide with each other. Specifically, the distance $D_b$ to the far point of the depth of field and the distance $D_f$ to the near point of the depth of field are respectively caused to coincide with the farthest point distance and the nearest point distance calculated by the distance estimation section 370. Therefore, the in-focus object plane position (distance) L and the effective diameter d of the lens are calculated by respectively substituting the farthest point distance and the nearest point distance for $D_b$ and $D_f$ in the expressions (19) and (20). The aperture value (F-number) is calculated by substituting the calculated effective diameter d of the lens into the expression (3).

The control value calculation section 380 outputs the calculated aperture value to the aperture control section 340, and outputs the calculated in-focus object plane position to the focus control section 390.

The aperture control section 340 controls the operation of the variable aperture 240 so that the aperture value decreases when the determination section 330 has determined that all of the segmented observation areas are in focus, in the same manner as in the first embodiment. The aperture control section 340 controls the operation of the variable aperture 240 so that the aperture value is set to the aperture value output from the control value calculation section 380 when the determination section 330 has determined that at least one of the segmented observation areas is out of focus. The aperture control section 340 notifies the dimmer section 360 of the aperture value so that the intensity of light applied to the object is kept constant even if the aperture value has changed. Specifically, the aperture control section 340 generates the aperture control signal based on the aperture value, and outputs the aperture control signal to the variable aperture 240 and the dimmer section 360.

The focus control section 390 controls the operation of the objective lens 230 so that the in-focus object plane position is set to the in-focus object plane position output from the control value calculation section 380. Specifically, the focus control section 390 generates the in-focus object plane position control signal based on the calculated in-focus object plane position, and outputs the in-focus object plane position control signal to the objective lens 230.

Although an example in which the control device is connected to the endoscope has been described above, another configuration may also be employed. For example, image information acquired by the endoscope may be transmitted to a server via a network, and may be processed by the server. Specifically, the control device 300 according to each embodiment may be a server, and may communicate with other elements via a wireless or cable network.

As shown in FIG. 10, the control device 300 according to the second embodiment further includes the focus control section 390 that controls the in-focus object plane position of the imaging optical system. The aperture control section 340 and the focus control section 390 respectively control the aperture and the in-focus object plane position of the imaging optical system so that the farthest point among the corresponding points in real space that respectively correspond to the segmented observation areas coincides with the far point of the depth of field, and the nearest point among the corresponding points in real space that respectively correspond to the segmented observation areas coincides with the near point of the depth of field (see the expressions (15) to (20)).

Specifically, the control device 300 further includes the distance estimation section 370. The distance estimation section 370 estimates a first distance from the imaging optical system to the farthest point and a second distance from the imaging optical system to the nearest point based on the pixel value of each pixel within the image of the object. The aperture control section 340 and the focus control section 390 respectively calculate the aperture value and the in-focus object plane position of the imaging optical system when the farthest point coincides with the far point of the depth of field and the nearest point coincides with the near point of the depth of field based on the first distance and the second distance.

This makes it possible to cause the depth of field of the imaging optical system to coincide with the target depth of field (i.e., cause the depth of field of the imaging optical system to coincide with the observation area). Therefore, the aperture can be opened up to a maximum extent while allowing the observation area to be included within the depth of field, so that a decrease in resolution due to a small aperture blur can be further suppressed as compared with the first embodiment.

The image of the object may be a color image that has an R channel, a G channel, and a B channel. The distance estimation section 370 may estimate the first distance and the second distance based on the pixel value of each pixel of the R channel.

This makes it possible to estimate the distance to the segmented observation area based on the R signal value. Absorption by hemoglobin occurs to only a small extent when using the R channel as compared with the G channel and the B channel. Therefore, the distance can be estimated with higher accuracy by utilizing the R channel.

4. Software

Although an example in which each section of the control device 300 is implemented by hardware has been described above, another configuration may also be employed. For example, a CPU may perform the process of each section on an image acquired by the imaging section. Specifically, the process of each section may be implemented by means of software by causing the CPU to execute a program. Alternatively, part of the process of each section may be implemented by software.

When implementing the process of each section of the control device 300 by software, the imaging section may be separately provided, and a known computer system (e.g., work station or personal computer) may be used as the control device. In this case, a program (control program) that implements the process of each section of the control device 300 may be provided in advance, and executed by the CPU of the computer system.

Figure 12:
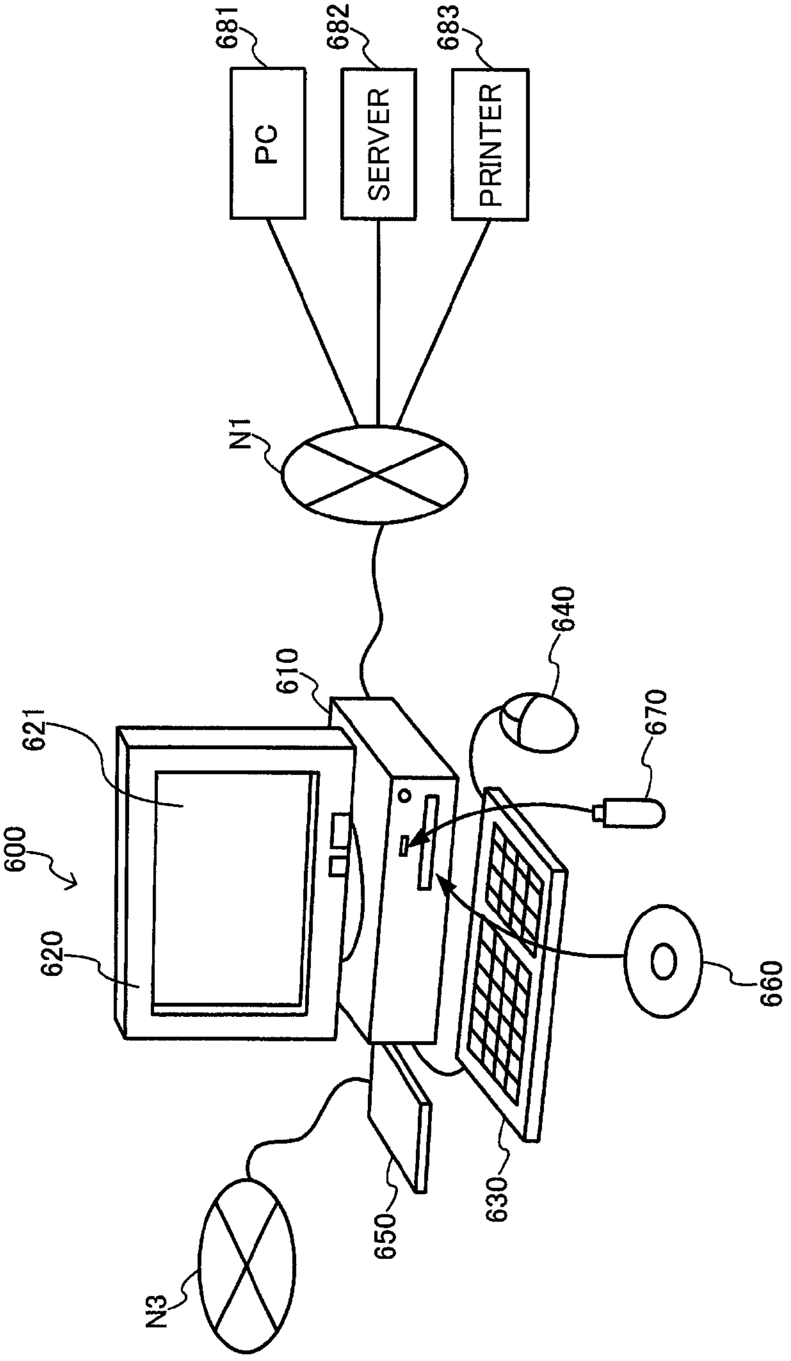
FIG. 12 is a system configuration diagram showing the configuration of a computer system.
Figure 13:
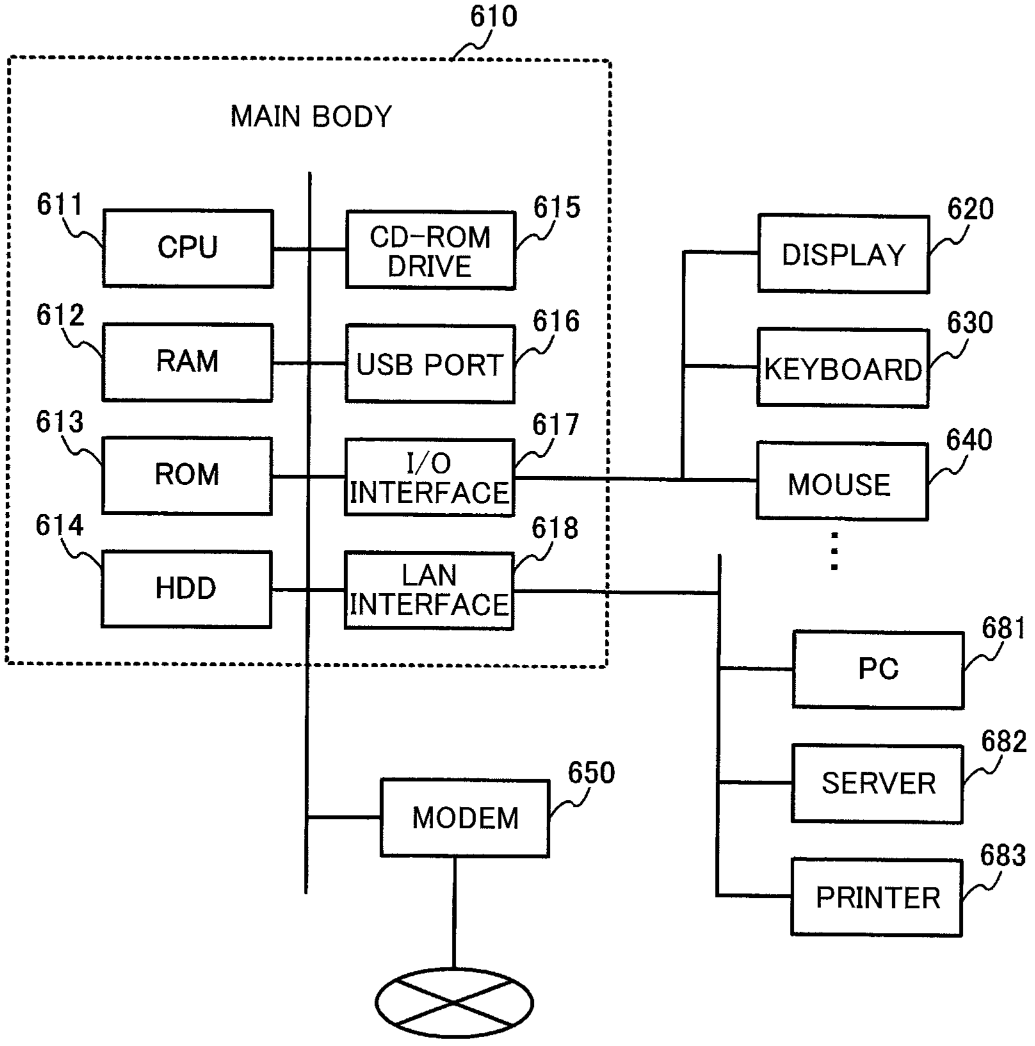
FIG. 13 is a block diagram showing the configuration of a main body included in a computer system.

FIG. 12 is a system configuration diagram showing the configuration of a computer system 600 according to a modification. FIG. 13 is a block diagram showing the configuration of a main body 610 of the computer system 600. As shown in FIG. 12, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As shown in FIG. 13, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to a personal computer (PC) 681 (i.e., another computer system), a server 682, a printer 683, and the like via the LAN interface 618 and the local area network or the large area network N1.

The computer system 600 implements the functions of the control device by reading an aperture control program (see FIG. 5, for example) recorded on a given recording medium, and executing the aperture control program. The given recording medium may be an arbitrary recording medium that records the aperture control program that can be read by the computer system 600, such as the CD-ROM 660, the USB memory 670, a portable physical medium (e.g., MO disk, DVD disk, flexible disk (FD), magnetooptical disk, or IC card), a stationary physical medium (e.g., HDD 614, RAM 612, or ROM 613) that is provided inside or outside the computer system 600, or a communication medium that temporarily stores a program during transmission (e.g., the public line N3 connected via the modem 650, or the local area network or the wide area network N1 to which the computer system (PC) 681 or the server 682 is connected).

Specifically, the aperture control program is recorded on a recording medium (e.g., portable physical medium, stationary physical medium, or communication medium) so that the aperture control program can be read by a computer. The computer system 600 implements the functions of the control device by reading the aperture control program from such a recording medium, and executing the aperture control program. Note that the aperture control program need not necessarily be executed by the computer system 600. The invention may be similarly applied when the computer system (PC) 681 or the server 682 executes the aperture control program, or the computer system (PC) 681 and the server 682 execute the aperture control program in cooperation.

The embodiments of the invention may also be applied to a computer program product that stores a program code that implements each section (e.g., image acquisition section, determination section, aperture control section, control section, and dimmer section) according to the embodiments of the invention.

The term "computer program product" refers to an information storage medium, a device, an instrument, a system, or the like that stores a program code, such as an information storage medium (e.g., optical disk medium (e.g., DVD), hard disk medium, and memory medium) that stores a program code, a computer that stores a program code, or an Internet system (e.g., a system including a server and a client terminal), for example. In this case, each element and each process according to the embodiments of the invention are implemented by corresponding modules, and a program code that includes these modules is recorded in the computer program product.

The embodiments of the invention and the modifications thereof have been described above. Note that the invention is not limited to the above embodiments and the modifications thereof. Various modifications and variations may be made without departing from the scope of the invention. A plurality of elements disclosed in connection with the above embodiments and the modifications thereof may be appropriately combined. For example, some of the elements disclosed in connection with the above embodiments and the modifications thereof may be omitted. Some of the elements disclosed in connection with different embodiments or modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. A control device comprising:

a processor comprising hardware, the processor implementing:

an image acquisition section configured to acquire an image captured by an imaging optical system;

a determination section comprising:

an observation area setting section configured to set an observation area within the image, wherein the observation area corresponds to a portion of an object shown in the image, the portion being positioned within a predetermined range of distances from the imaging optical system, and wherein the observation area is set according to pixels of the image having pixel values within a predetermined range of values corresponding to the predetermined range of distances;

a division section configured to divide the observation area within the image into a plurality of segmented observation areas, wherein the plurality of segmented observation areas correspond to a plurality of segments of the portion of the object shown in the image, and wherein each of the plurality of segments is positioned within a different segment of the predetermined range of distances from the imaging optical system; and an in-focus determination section configured to determine whether or not one or more of the plurality of segmented observation areas is in focus; and an aperture control section configured to control an aperture of the imaging optical system based on a result of the determination of whether or not one or more of the plurality of the segmented observation areas is in focus, wherein the aperture control section is configured to increase an aperture value of the aperture when the in-focus determination section has determined that at least one of the plurality of segmented observation areas is out of focus, and wherein the aperture control section is configured to control the aperture of the imaging optical system so that corresponding points in real space that respectively correspond to the plurality of segmented observation areas are included within a depth of field of the imaging optical system when the in-focus determination section has determined that at least one of the plurality of segmented observation areas is out of focus.

2. The control device according to claim 1, wherein the aperture control section is configured to decrease an aperture value of the aperture when the in-focus determination section has determined that all of the plurality of segmented observation areas are in focus.

3. The control device according to claim 1, wherein the aperture control section is configured to control the aperture of the imaging optical system so that at least a farthest point and a nearest point among the corresponding points in real space that respectively correspond to the plurality of segmented observation areas are included within the depth of field of the imaging optical system.

4. The control device according to claim 3, wherein the aperture control section is configured to control the aperture of the imaging optical system so that the farthest point coincides with a far point of the depth of field or the nearest point coincides with a near point of the depth of field.

5. The control device according to claim 3, wherein the processor further implements a focus control section configured to control an in-focus object plane position of the imaging optical system, wherein the aperture control section is configured to control the aperture of the imaging optical system so that the farthest point coincides with a far point of the depth of field, and the nearest point coincides with a near point of the depth of field, and wherein the focus control section is configured to control the in-focus object plane position of the imaging optical system so that the farthest point coincides with the far point of the depth of field, and the nearest point coincides with the near point of the depth of field.

6. The control device according to claim 5, wherein the processor further implements a distance estimation section configured to estimate a first distance from the imaging optical system to the farthest point and a second distance from the imaging optical system to the nearest point based on the pixel value of each pixel within the image of the object, wherein the aperture control section is configured to calculate an aperture value of the imaging optical system when the farthest point coincides with the far point of the depth of field and the nearest point coincides with the near point of the depth of field based on the first distance and the second distance, and wherein the focus control section is configured to calculate the in-focus object plane position of the imaging optical system when the farthest point coincides with the far point of the depth of field and the nearest point coincides with the near point of the depth of field based on the first distance and the second distance.

7. The control device according to claim 1, wherein the aperture control section is configured to control the aperture of the imaging optical system so that a depth of field of the imaging optical system is equal to or greater than a distance between a nearest point and a farthest point among corresponding points in real space that respectively correspond to the plurality of segmented observation areas when the in-focus determination section has determined that at least one of the plurality of segmented observation areas is out of focus.

8. The control device according to claim 1, wherein the aperture control section is configured to set a change prohibition period in which a change in an aperture value is prohibited when the in-focus determination section has previously determined that all of the plurality of segmented observation areas are in focus, and has currently determined that segmented observation areas among the plurality of segmented observation areas in a number equal to or larger than a given number are out of focus, and wherein the aperture control section is configured to not change the aperture value until the change prohibition period elapses.

9. The control device according to claim 1, wherein the aperture control section is configured to increase an aperture value of the aperture of the imaging optical system when the in-focus determination section has determined that each of the plurality of segmented observation areas is out of focus.

10. The control device according to claim 1, wherein the processor is further configured to implement a reception section configured to receive, from a user, information that specifies the predetermined range of values for setting the observation area within the image, and wherein the observation area setting section is configured to set the observation area based on the received information.

11. The control device according to claim 1, wherein the image of the object is a color image that has an R channel, a G channel, and a B channel, wherein the in-focus determination section comprises a contrast calculation section configured to calculate contrast of at least one of the G channel and the B channel, and wherein the in-focus determination section is configured to determine whether or not the one or more of the plurality of segmented observation areas is in focus based on the calculated contrast.

12. The control device according to claim 6, wherein the image of the object is a color image that has an R channel, a G channel, and a B channel, and wherein the distance estimation section is configured to estimate the first distance and the second distance based on the pixel value of each pixel of the R channel.

13. The control device according to claim 1, wherein the imaging optical system is configured to variably set an imaging magnification of the object, and wherein the aperture control section is configured to control an aperture value of the aperture corresponding to the imaging magnification.

14. The control device according to claim 13, wherein the aperture control section is configured to control the aperture value based on an in-focus object plane distance or an in-focus object plane position of the imaging optical system that has changed corresponding to the imaging magnification so that the imaging optical system has a given depth of field.

15. The control device according to claim 1, wherein the processor further implements a dimmer section configured to control an intensity of light applied to the object, and wherein the dimmer section is configured to control the intensity of light based on an aperture value of the aperture.

16. An endoscope apparatus comprising:

the imaging optical system; and the control device according to claim 1.

17. An aperture control method comprising:

acquiring an image captured by an imaging optical system;

setting an observation area within the image, wherein the observation area corresponds to a portion of an object shown in the image, the portion being positioned within a predetermined range of distances from the imaging optical system, and wherein the observation area is set according to pixels of the image having pixel values within a predetermined range of values corresponding to the predetermined range of distances;

dividing the observation area within the image into a plurality of segmented observation areas, wherein the plurality of segmented observation areas correspond to a plurality of segments of the portion of the objection shown in the image, and wherein each of the plurality of segments is positioned within a different segment of the predetermined range of distances from the imaging optical system;

determining whether or not one or more of the plurality of segmented observation areas is in focus; and controlling an aperture of the imaging optical system based on a result of the determination of whether or not one or more of the plurality of the segmented observation areas is in focus, wherein the controlling the aperture comprises:

increasing an aperture value of the aperture when a determination is made that at least one of the plurality of segmented observation areas is out of focus, and controlling the aperture of the imaging optical system so that corresponding points in real space that respectively correspond to the plurality of segmented observation areas are included within a depth of field of the imaging optical system when the determination is made that at least one of the plurality of segmented observation areas is out of focus.

18. A non-transitory information storage medium storing a program that causes a computer to function as:

an image acquisition section configured to acquire an image captured by an imaging optical system;

an observation area setting section configured to set an observation area within the image, wherein the observation area corresponds to a portion of an object shown in the image, the portion being positioned within a predetermined range of distances from the imaging optical system, and wherein the observation area is set according to pixels of the image having pixel values within a predetermined range of values corresponding to the predetermined range of distances;

a division section configured to divide the observation area within the image into a plurality of segmented observation areas, wherein the plurality of segmented observation areas correspond to a plurality of segments of the portion of the object shown in the image, and wherein each of the plurality of segments is positioned within a different segment of the predetermined range of distances from the imaging optical system;

an in-focus determination section configured to determine whether or not one or more of the plurality of segmented observation areas is in focus; and an aperture control section configured to control an aperture of the imaging optical system based on a result of the determination of whether or not one or more of the plurality of the segmented observation areas is in focus, wherein the aperture control section is configured to increase an aperture value of the aperture when the in-focus determination section has determined that at least one of the plurality of segmented observation areas is out of focus, and wherein the aperture control section is configured to control the aperture of the imaging optical system so that corresponding points in real space that respectively correspond to the plurality of segmented observation areas are included within a depth of field of the imaging optical system when the in-focus determination section has determined that at least one of the plurality of segmented observation areas is out of focus.

* * * * *